United States Patent [19]
Kovačević et al.

[11] Patent Number: 5,250,525
[45] Date of Patent: Oct. 5, 1993

[54] 4-OXO-AZETIDINE-2-SULFONIC ACIDS AND THEIR SALTS, PROCESSES FOR THE PREPARATION THEREOF AND THEIR USE

[75] Inventors: Miće Kovačević; Zorica Mandić; Mirjana Tomić; Zinka Brkić; Jure J. Herak; Irena Lukić, all of Zagreb, Yugoslavia

[73] Assignee: Pliva Handels GmbH, Croatia

[21] Appl. No.: 833,856

[22] Filed: Feb. 11, 1992

[30] Foreign Application Priority Data
Feb. 12, 1991 [YU] Yugoslavia ............... 250/91
Aug. 12, 1991 [YU] Yugoslavia ............... 1390/91

[51] Int. Cl.[5] ............... C07D 205/09; C07D 205/095; C07D 417/12; A61K 31/395
[52] U.S. Cl. .................. 514/210; 540/355; 540/359
[58] Field of Search ............. 540/359, 354; 514/210

[56] References Cited
PUBLICATIONS
Herak, Croat. Chemica Acta 62(3) 521 (1989).

Primary Examiner—Mark L. Berch
Attorney, Agent, or Firm—Pollock, Vande Sande & Priddy

[57] ABSTRACT

The invention relates to novel 4-oxo-azetidine-2-sulfonic acids and their salts or the formula I

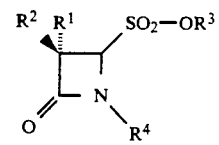

wherein:
$R^1$ = hydrogen, halogen, phenylacetamido;
$R^2$ = hydrogen, halogen, phenylacetamido, phenoxyacetamido, phthalimido, 5-methyl-3-o-chlorophenyl-isoxazole-4-carboxamido;
$R^3$ = hydrogen, alkali metal, alkaline earth metal, quaternary ammonium group;
$R^4$ = hydrogen, $SO_2O^- + NBu_4$-n, $(CH_3)_2C=C-COOCH_3$, $(CH_3)_2C=C-COOCH_2$-Ph, $(CH_3)_2C=C-COOCH_2-C_6H_4-NO_2$-p, $(CH_3)_2C=C-COOCH_2-C_6H_4-CH_3$-m.

The products (I) may be used as intermediates in the synthesis of beta-lactamic antibiotics or as components in antimicrobial preparations.

25 Claims, No Drawings

4-OXO-AZETIDINE-2-SULFONIC ACIDS AND THEIR SALTS, PROCESSES FOR THE PREPARATION THEREOF AND THEIR USE

The present invention relates to novel 4-oxo-azetidine-2-sulfonic acids and their salts, to processes for the preparation thereof, and to their use in the preparation of pharmaceuticals, or as active ingredients in pharmaceuticals.

These are known numerous monocyclic 4-oxo-azetidine-1-sulfonic acids and derivatives thereof/Chemistry in Britain (1983) 302/, comprising the important beta-lactamic antibiotic Aztreonam/Drugs of the Future 8 (1983) 295/.

There are known also some 4-oxo-azetidine-2-sulfonic acids, obtained by the transformation of bicyclic molecules/Angew.Chem. 95 (1983) 912/.

According to the data on Prior Art, known to the Applicant, there have not been known 4-oxo-azetidine-2-sulfonic acids and their salts, processes for the obtaining thereof as well as their use, which are the object of the present invention.

One object of the present invention are novel 4-oxo-azetidine-2-sulfonic acids and their salts of the general formula I

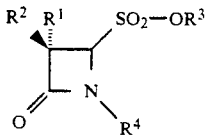

wherein the radicals have the meanings:
$R^1$ = hydrogen, halogen, phenylacetamido;
$R^2$ = hydrogen, halogen, phenylacetamido, phenoxyacetamido, phthalimido, 5-methyl-3-o-chlorophenyl-isoxazole-4-carboxamido;
$R^3$ = hydrogen, alkali metal, alkaline earth metal, quaternary ammonium group;
$R^4$ = hydrogen, $SO_2O^{-+}NBu_4$-n, $(CH_3)_2C=C-COOCH_3$, $(CH_3)_2C=C-COOCH_2$-Ph, $(CH_3)_2C=C-COOCH_2-C_6H_4-NO_2$-p, $(CH_3)_2C=C-COOCH_2-C_6H_4-CH_3$-m.

A further object of the present invention is a process for the preparation of the novel 4-oxo-azetidine-2-sulfonic acids and salts of the general formula I, wherein the radicals have the afore-said meanings, which is performed by:

subjecting 4-oxo-azetidine-2-sulfinic acids and their derivatives of the formula II

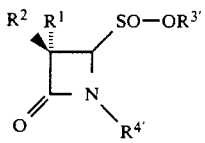

wherein the radicals have the meanings:
$R^1$ = hydrogen, halogen, phenylacetamido;
$R^2$ = hydrogen, halogen, phenylacetamido, phenoxyacetamido, phthalimido, 5-methyl-3-o-chlorophenyl-isoxazole-4-carboxamido;
$R^{3'}$ = hydrogen, alkali metal atom, or alkaline earth metal atom, alkyl, aralkyl or aryl;
$R^{4'}$ = hydrogen, $(CH_3)_2C=C-COOCH_3$, $(CH_3)_2C=C-COOCH_2$-Ph, $(CH_3)_2C=C-COOCH_2-C_6H_4-NO_2$-p, $(CH_3)_2C=C-COOCH_2-C_6H_4-CH_3$-m, to oxidation with hydrogen peroxide, peracetic acid, m-chloroperbenzoic acid or potassium permanganate, in an acidic or neutral, aqueous or aqueous-organic medium at a temperature of 0° to 80° C., and optionally, the obtained product of the above formula II, wherein $R^{3'}$ stands for an alkyl, aralkyl or aryl group, whereas, the radicals $R^1$, $R^2$ and $R^{4'}$ have the above-cited meanings, is hydrolized in an acidic or mildly alkaline, aqueous or aqueous-organic medium, or in an organic medium, under addition of inorganic salts or organic bases, and optionally, the obtained product of the above formula II, wherein $R^{3'}$ stands for hydrogen, whereas, the radicals $R^1$, $R^2$, and $R^{4'}$ have the above-cited meanings, is subjected to disproportionation/oxidation in an acidic or neutral, aqueous or aqueous-organic medium by exposing to the atmospheric air for a prolonged period at room temperature, and finally, the obtained products are optionally converted into their salts.

The starting compounds (II) are easily available (Croat.Chem.Acta. 62 (1989) 521.

The 4-oxo-azetidine-2-sulfonic acids of the present invention are isolated by conventional methods, and identified in the form of free acids or salts with inorganic or organic acids.

A further object of the present invention is the use of the novel compounds (I) as useful starting substances or intermediates in the preparation of various beta-lactamic analogues, especially of the Monobactam or Carbapenem series, several of which are chemotherapeutical agents.

A further object of the present invention is the use of the novel substances (I) in compositions of antimicrobial activity, or as components, demonstrating a synergistic activity in combination with other antimicrobial agents.

The present invention is illustrated, but in no way limited, by the following Examples.

EXAMPLE 1

(2R, 3R) 3-Phthalimido-1-(1'-p-nitrobenzyloxycarbonyl-2'-methyl-prop-1'-enyl)-4-oxo-azetidine-2-sulfonic acid a) The methyl ester of 3-phthalimido-1-(1'-p-nitrobenzyloxycarbonyl-2'-methyl-prop-1'-enyl)-4-oxo-azetidine-2-sulfinic acid (1230 mg; 2.33 mmole) was dissolved in ethyl acetate (30 mL) and water (12 mL), there was added 80% acetic acid (0.3 mL) and at +5° C. there was added drop-by-drop during 80 minutes 14 mL of aqueous solution of $KMnO_4$ (560 mg; 3.5 mmole). Upon addition of water (30 mL) there was added drop-by-drop 30% $H_2O_2$ (about 7 mL) till the disappearance of the color. The organic layer was separated, and upon addition of a solution of $NaHCO_3$ (250 mg, 3 mmole) in water there was stirred at 50° C. There was evaporated in vacuum into a solid residue, which was dissolved in water and eluted on Dowex 50. The eluate was lyophilized. There was obtained 941 mg (76.3%) of a flaky residue.

Rf 0.51 ($EtoAc:HAc:H_2O = 10:2:1$);

IR (KBr): 3700–3200 bm, 1790 s, 1770 s, 1725 vs, 1520 m, 1395 s, 1350 m, 1215 m, 1040 w (cm$^{-1}$)

$^1$H NMR (DMSO-d6) δ: 2.33 (s, 2 $CH_3$); 4.81 (d, $C_2H$, J 5.4 Hz); 4.97 (s, $SO_2OH + HOH$); 5.44 (d, $C_3H$, J 5.4

Hz); 5.50 (s, OCH$_2$); 7.81 and 8.35 (2d, C$_6$H$_4$NO$_2$); 7.97 (s, Pht) (ppm)

b) The methyl ester of 3-phthalimido-1-(1'-p-nitrobenzyloxycarbonyl-2'-methyl-prop-1'-enyl)-4-oxo-azetidine-2-sulfonic acid (480 mg, 0.88 mmole) was dissolved in methylenechloride (10 mL), there was added triethylamine (200 mg, 1.98 mmole) and stirred for 4 hours at +5° C. Upon evaporation till dryness the residue was dissolved in water and eluted on Dowex 50. The eluate was lyophilized, leaving a flaky product, identical to the product, described in the above process a).

EXAMPLE 2

(2R, 3R) 3-Phenylacetamido-1-(1'-p-nitrobenzyloxycarbonyl-2'-methyl-prop-1'-enyl)-4-oxo-azetidine-2-sulfonic acid a) The methyl ester of 3-phenylacetamido-1-(1'-p-nitrobenzyloxycarbonyl-2'-methyl-prop-1'-enyl)-4-oxo-azetidine-2-sulfinic acid (400 mg, 0.78 mmole) was dissolved in methylenechloride (15 mL) and formic acid (1.3 mL), whereupon there was added at room temperature 30% hydrogen peroxide (4.8 mL). The reaction mixture was stirred for 2 hours at 40° C., whereupon there was added methylenechloride (20 mL) and water (15 mL). The organic extract was separated, washed with water (1×15 mL), dried (Na$_2$SO$_4$), filtered and evaporated in vacuum till dryness. The residue was dissolved in ethyl acetate (10 mL) and upon addition of triethylamine (100 mg, 1 mmole) there was stirred for 1.5 hours at room temperature. There was evaporated in vacuum, the residue was dissolved in water (10 mL), eluted on Dowex 50 and lyophilized. The residue was 213 mg (52.6%) of a crude product, which was crystallized from ethyl acetate.

M.p.=164°-166° C.
Rf=0.58(CH$_2$Cl$_2$: CH$_3$OH=4:1)
IR (KBr): 3700-3150 bm, 3360 s, 1765 s, 1755 s, 1710 m, 1680 m, 1660 m, 1520 s, 1350 s, 1220 vs, 1040 s (cm$^{-1}$)
$^1$H NMR (DMSO-d6) δ: 2.04 (s, CH$_3$); 2.18 (s, CH$_3$); 3.52 (s, CH$_2$CO); 4.59 (d, C$_2$H, J 5.4 Hz); 5.33 (s, O—CH$_2$); 5.37 (q, C$_3$H, J 5.4 and 10.1 Hz); 6.44 (bs, SO$_2$OH); 7.27 (s, C$_6$H$_5$); 7.67 and 8.23 (2d, C$_6$H$_4$—NO$_2$, J 8.6 Hz) and 8.0 (d, NHCO, J 10.1 Hz); (ppm)

b) The methyl ester of 3-phenylacetamido-1-(1'-p-nitrobenzyloxycarbonyl-2-methylprop-1'-enyl)-4-oxo-azetidine-2-sulfonic acid (240 mg, 0.45 mmole) was dissolved in methylenechloride (5 mL); there was added triethylamine (68 mg, 0.67 mmole) and the reaction solution was stirred for one hour. There was evaporated in vacuum, the residue was dissolved in water (10 mL), eluted on Dowex 50 and lyophilized. The residue was identical to the product, as obtained in the above process a).

The yield: 180 mg (77.8%).

EXAMPLE 3

Sodium salt of (2R, 3R) 3-phenylacetamido-4-oxo-azetidine-2-sulfonic acid

The methyl ester of 3-phenylacetamido-1-(1'-p-nitrobenzyloxycarbonyl-2-methylprop-1'-enyl)-4-oxo-azetidine-2-sulfinic acid (3.00 g, 5.82 mmole) was dissolved in ethyl acetate (40 mL), cooled to a temperature of 0° C., and upon addition of 80% acetic acid (40 mL) and dropwise addition of an aqueous solution of potassium permanganate (75 mL, 18.98 mmole), under stirring within 40 minutes and kept stirring for additional 20 minutes. There was added drop-by-drop a solution of 30% H2O2 (2.5 mL) which resulted in the disappearance of the permanganate color. Upon addition of ethyl acetate (50 mL) and sodium chloride until the saturation of the aqueous solution there was stirred for 30 minutes at room temperature. The organic extract was separated and the aqueous layer extracted with ethyl acetate (40 mL). The organic extracts were combined, dried (Na$_2$SO$_4$), filtered and evaporated in vacuum till dryness. Upon addition of ethyl acetate to the residue the suspension was stirred for 2 hours at +5° C. and the crystals were aspirated.

The yield: 640 mg (35.9%).
M.p.=205°-207° C.
Rf=0.61 (n-BuOH:HAc:H$_2$O=4:1:1)
IR (KBr): 3310 m, 3325 m, 1760 vs, 1640 s, 1525 s, 1260 s, 1205 s, 1070 s (cm$^{-1}$)
$^1$H NMR (DMSO-d6) δ: 3.59 (s, CH$_2$CO); 4.39 (d, C$_2$H, J 5.0 Hz); 5.40 (q, C$_3$H, J 5.0 and 10.2 Hz); 7.38 (s, C$_6$H$_5$); 7.93 (d, NHCO, J 10.2 Hz); 8.88 (bs, N$_1$H) (ppm)
Calc.: Na 7.51%. Found: Na 7.68%.

EXAMPLE 4

Tetrabutylammonium salt of (2R, 3R) 3-phenylacetamido-4-oxo-azetidine-2-sulfonic acid The sodium salt of 3-phenylacetamido-4-oxo-azetidine-2-sulfonic acid (100 mg, 0.33 mmole) and tetrabutylammonium hydrogen sulfate (120 mg, 0.35 mmole) were dissolved in a mixture of CH$_2$Cl$_2$ (10 mL) and H$_2$O (10 mL) and stirred for 2 hours at room temperature. The organic extract was separated; the aqueous portion was extracted with CH$_2$Cl$_2$ (2×10 mL). The combined organic extracts were dried (Na$_2$SO$_4$), filtered and evaporated in vacuum. The residue: 100 mg (57.6%) of the product.

Rf=0.58 (CH$_2$Cl$_2$: CH$_3$OH=4:1)
IR (KBr): 3325 w, 2960 s, 2880 m, 1770 vs, 1680 s, 1520 m, 1225 s, 1200 s (cm$^{-1}$)
$^1$H NMR (CDCl$_3$) δ: 103-1.54 (28H, m); 3.12-3.30 (8H, m); 3.59 (s, CH$_2$CO); 4.58 (d, C$_2$H, J 5.3 Hz); 5.63 (q, C$_3$H, J 5.3 and 10.5 Hz); 7.30 (s, C$_6$H$_5$); 7.76 (d, CONH, J 10.0 Hz); 8.20 (d, N$_1$H, J 8.0 Hz) (ppm)

EXAMPLE 5

Tetrabutylammonium salt of (2R, 3R) 3-phenylacetamido-4-oxo-azetidine-1,2-disulfonic acid The methyl ester of (2R, 3R) 3-phenylacetamido-4-oxo-azetidine-2-sulfonic acid (160 mg, 0.54 mmole) was added to a mixture of the complex of pyridine and sulfur trioxide (85 mg, 0.54 mmole) and triethylamine (0.12 mL) in methylenechloride (10 mL). The reaction solution was stirred for 2 hours at room temperature in a nitrogen stream and poured into a 1M solution of KH$_2$PO$_4$ (10 mL). The aqueous portion was separated, washed with methylenechloride (10 mL) and stirred with a solution of tetrabutylammonium hydrogen sulfate (180 mg, 0.54 mmole) in methylenechloride (30 mL) for 2 hours at room temperature. The organic extract was separated, whereas, the aqueous layer was washed with methylenechloride (2×10 mL). The combined organic extracts were dried (Na$_2$SO$_4$), filtered and evaporated.

The residue: 140 mg of the product (30.6%).
Rf=0.56 (CH$_2$Cl$_2$: MeOH=4:1)
IR (CH$_2$Cl$_2$): 3400 w, 2920 s, 2850 s, 1775 s, 1675 s, 1510 m, 1220 s, 885 s (cm$^{-1}$)

$^1$H NMR (CDCl$_3$) δ: 1.00–1.65 (56H, m); 3.13–3.23 (16H, m); 3.56 (s, CH$_2$CO); 4.54 (d, C$_2$H, J 5.0); 5.60 (q, C$_3$H, J 5.0 and 10.3 Hz); 7.27 (s, C$_6$H$_5$); 7.73 (d, CONH, J 10.3 Hz) (ppm)

EXAMPLE 6

Tetrabutylammonium salt of (2R, 3S) 3-phenyl-acetamido 4-oxo-azetidine-2-sulfonic acid The methyl ester of (2R, 3S) 3-phenylacetamido-1-(1'-p-nitrobenzyloxycarbonyl-2'-methyl-prop-1'-enyl)-4-oxo-azetidine-2-sulfinic acid (515 mg, 1 mmole) was dissolved in ethyl acetate (10 mL), cooled to a temperature of 0° C., there was added a solution of 80% acetic acid (6.8 mL) and drop-by-drop a 4% solution of KMnO$_4$ (11.8 mL, 3 mmole) under vigorous stirring during 1 hour. Then a 30% solution of H$_2$O$_2$ was added drop-by-drop till the decolorization of the reaction solution. Then ethyl acetate (20 mL) and NaCl were added till the saturation of the aqueous solution and stirred for further 30 minutes at room temperature. The organic extract was separated, whereas, the aqueous layer was once more extracted with ethyl acetate (20 mL). The combined organic extracts were dried (Na$_2$SO$_4$), filtered and evaporated till dryness. Upon addition of ethyl acetate-methanol there was obtained a suspension which was filtered and the obtained precipitate was dissolved in water (10 mL) and fed over Dowex 50. The obtained aqueous solution (20 mL) was stirred for 2 hours with tetrabutylammonium hydrogen sulfate in CH$_2$Cl$_2$ (20 mL) (170 mg, 0.5 mmole). The organic extract was separated, whereas, the aqueous layer was extracted with CH$_2$Cl$_2$ (2×10 mL). The combined organic extracts are dried (Na$_2$SO$_4$), filtered, and evaporated.

Yield: 94 mg (18%).
Rf=0.51 (CH$_2$Cl$_2$: MeOH=4:1)
IR (KBr): 3320 w, 2950 s, 2920 s, 1765 s, 1675 s, 1520 m, 1220 s, 1190 s (cm$^{-1}$)

EXAMPLE 7

(2R, 3R) 3-Phenoxyacetamido 4-oxo-azetidine-2-sulfonic acid

The methyl ester of 3-phenoxyacetamido-1-(1'-methyloxycarbonyl-2'-methyl-prop-1'-enyl)-4-oxo-azetidine-2-sulfinic acid (4.1 g, 10 mmole) was dissolved in ethyl acetate (100 mL) and 80% acetic acid (40 mL) and at 0° C. there was added drop-by-drop a 4% aqueous solution of KMnO$_4$ (150 mL, 6 g, 38 mmole) within 60 minutes. The reaction suspension was stirred for further 60 minutes at 0° C. Upon addition of water (20 mL), there was added drop-by-drop 30% H$_2$O$_2$ (5 mL) till the disappearance of the color. The organic layer was separated, dried over Na$_2$SO$_4$ and evaporated under reduced pressure into a solid residue. There was obtained 3.9 g of a solid material to which methanol (30 mL) was added; upon stirring for 60 minutes the solid was separated by filtration.

Yield: 0.96 g (32%)
M.p.: 225°–230° C. (decomp.)
Rf=0.45 (n-BuOH:HAc:H$_2$O=4:1:1)
IR (KBr): 3330–3315 m, 1750 vs, 1655 s, 1595 m, 1525 m, 1495 m, 1245–1195 s, 1060 s, 750 m (cm$^{-1}$)
$^1$H NMR (DMSO-d6) δ: 4.31 (d, C$_2$H, J 4.98 Hz); 4.50 (s, OCH$_2$); 5.35 (q, C$_3$H, J 4.98 Hz and 9.96 Hz); 7.02–7.40 (m, C$_6$H$_5$); 8.58 (d, NH-CO, J 9.96 Hz) and 8.82 (s, N$_1$H) (ppm)

EXAMPLE 8

(2R, 3R) 3-Phenoxyacetamido-1-(1'-methyloxycarbonyl-2'-methyl-prop-1'-enyl)-4-oxo-azetidine-2-sulfonic acid The mother liquor upon the isolation of the solid material in the process, described in Example 7, was evaporated under reduced pressure into a solid residue. Upon addition of methanol (5 mL) and acetone (30 mL), there was stirred for 60 minutes. The solid was separated by filtration, dissolved in water (10 mL) and fed over Dowex 50. The eluate was lyophilized.

Yield: 1.32 g (32%)
Rf=0.70 (n-BuOH:HAc:H$_2$O=4:1:1)
IR (KBr): 3350 m, 1780 s, 1705 s, 1600 w, 1540 m, 1500 m, 1440 m, 1390 w, 1230 s, 1035 m (cm$^{-1}$)
$^1$H NMR (DMSO-d6) δ: 2.11 (s, CH$_3$); 2.28 (s, CH$_3$); 3.82 (s, —OCH$_3$); 4.67 (s, OCH$_2$); 4.7 (d, C$_2$H, J 5.6 Hz); 5.37 (s, SO$_2$OH+HOH); 5.57 (q, C$_3$H, J 5.6 Hz and 8.8 Hz); 7.02–7.52 (m, C$_6$H$_5$O) and 8.83 (d, NH, J 8.8 Hz) (ppm)

EXAMPLE 9

Tetrabutylammonium salt of (2R, 3R) 3-Phenoxyacetamido-4-oxo-azetidine-2-sulfonic acid (2R, 3R) 3-Phenoxyacetamido-4-oxo-azetidine-2-sulfonic acid (0.3 g, 1 mmole) was dissolved in water (10 ml), and there was added tetrabutylammonium hydrogen sulfate (0.34 g, 1 mmole) and methylenechloride (10 mL). The mixture was stirred for 3 hours at room temperature. The organic layer was separated, washed with water (10 mL) and evaporated under reduced pressure.

Yield: 0.39 g (72%).
Rf=0.80 (CH$_2$Cl$_2$: MeOH=4:1)
IR (paraffin oil): 3350–3110 m, 3000–2850 s, 1680 s, 1600 w, 1530 m, 1495 s, 1460 m, 1380 m, 1225 vs, 1185 s, 1060 s, 1010 m (cm$^{-1}$)
Analysis: C$_{27}$H$_{47}$N$_2$O$_6$S (541.736): Calc.: C 59.84; H 8.74; N 7.76; S 5.92. Found: C 59.81; H 9.98; N 7.81; S 5.06.
$^1$H NMR (DMSO-d6) δ: 1.00–1.84 (m, 28H); 3.20–3.5 (m, 8H); 4.46 (d, C$_2$H, J 5.3 Hz); 4.62 (s, OCH$_2$); 5.47 (q, C$_3$H, J 5.3 Hz and 10.25 Hz); 7.02–7.53 (m, C$_6$H$_5$O); 8.7 (d, NHCO, J 10.25 Hz); and 8.95 (s, N$_1$H) (ppm)

EXAMPLE 10

(2R, 3R) 3-(3'-o-chlorophenyl-5'-methyl-isoxazole-4'-carboxamido)-1-(1'-m-methylbenzyl-oxycarbonyl-2'-methyl-prop-1'-enyl)-4-oxo-azetidine-2-sulfonic acid a) The methyl ester of 3-(3'-o-chlorophenyl-5'-methyl-isoxazole-4'-carboxamido)-1-(1'-m-methyl-benzyl-oxycarbonyl-2'-methyl-prop-1'-enyl)-4-oxo-azetidine-2-sulfinic acid (703 mg, 1.2 mmole) was dissolved in CHCl$_3$ (8 mL) and there was added to the solution under stirring a solution of m-chloroperbenzoic acid (414 mg, 2.4 mmole) in CHCl$_3$ (5 mL). The reaction mixture was stirred at room temperature for 10 hours, and treated with a saturated aqueous solution of NaHCO$_3$ (10 mL) and water. The organic layer was evaporated under reduced pressure into a foamy solid. Upon chromatography on a silica gel column by means of solvents methylenechloride-methanol, there was isolated:

438 mg (65.4%) of the corresponding sulfonic acid of a

Rf=0.42 (CH$_2$Cl$_2$: MeOH=4:1);
M.p.=178°-182° C.

IR (KBr): 3700-3150 bs, 1780 s, 1600 s, 1610 m, 1530 m, 1400 w, 1295 w, 1220 vs, 1040 m, 770 m (cm$^{-1}$)

$^1$H NMR (CDCl$_3$) δ: 1.62 and 1.82 (2s, (CH$_3$)$_2$); 2.04 (s, CH$_3$-isoxazole); 2.31 (s, CH$_3$—Ph); 2.71 (s, b SO$_3$H); 4.40 (d, J 6 Hz, C$_2$H); 4.48 (s, CH$_2$); 4.89 (dd, J 6 and 8 Hz, C$_3$H); 6.04 (d, J 8 Hz, NH); 6.18-6.31 (m, Ph), 6.40-6.62 (m, Ph-isoxazole)

b) There was prepared a solution of the methyl ester of 3-(3'-o-chlorophenyl-5'-methyl-isoxazole-4'-carboxamido)-1-(1'-m-methyl-benzyl-oxycarbonyl-2'-methyl-prop-1'-enyl)-4-oxo-azetidine-2-sulfinic acid (1.85 g, 3 mmole) in acetic acid (26 mL) there was added H$_2$O$_2$ (6.6 mL, 60 mmole) and stirred at room temperature for 15 hours. The reaction mixture was poured into cold water (100 mL) and the obtained solution was neutralized (pH about 5) by addition of solid NaHCO$_3$, and extracted with methylenechloride (2×100 mL). The organic extracts were combined and evaporated under reduced pressure into a foamy solid. Upon chromatography on a silica gel column by means of a solvent mixture methylenechloride-methanol there was isolated 1.160 g (77.5%) of a compound, which was identical with the product, obtained in the above process a).

c) The methyl ester of (3'-o-chlorophenyl-5'-methyl-isoxazole-4'-carboxamido)-1-(1'-m-methyl-benzyloxycarbonyl-2'-methyl-prop-1'-enyl)-4-oxo-azetidine-2-sulfinic acid (1.030 g, 1.8 mmole) was dissolved in ethyl acetate (10 mL), and there was added acetic acid (1.2 mL). Under stirring there was added to the solution drop-by-drop an aqueous solution of 4% KMnO$_4$ at a temperature of +10° C. till a pink color was observed. The solution was discolored by addition of H$_2$O$_2$ and the layers were separated. Upon washing with a saturated solution of NaHCO$_3$ and water the organic portion was evaporated under reduced pressure into a thick, nearly colorless liquid. Upon separation of the components on a silica gel column by means of the solvent mixture methylenechloride-methanol, there was isolated 180 mg (21%) of a substance, which was identical with a substance of the above process a).

Sodium salt of 2R-1-(1'-benzyloxycarbonyl-2'methyl-prop-1'-enyl-)-4-oxo-azetidine-2-sulfonic acid

EXAMPLE 11

The methyl ester of 2R-1-(1'-benzyloxycarbonyl-2'-methyl-prop-1'-enyl)-4-oxo-azetidine-2-sulfonic acid (2.585 g, 7.32 mmole) was dissolved in ethyl acetate (40 mL), there was added water (40 mL) and stirred for 5 hours at boiling. The reaction mixture was cooled and the layers were separated. The aqueous layer was once more extracted with ethyl acetate (30 mL).

The aqueous portion was overlayered with ethyl acetate (30 mL) and the pH was adjusted to 7.5 with solid sodium hydrogen carbonate. To the reaction mixture was added sodium chloride till saturation. The layers were separated, and the aqueous layer was once more extracted with ethyl acetate (2×20 mL). The combined ethyl acetate layers were washed with water which was saturated with sodium chloride (20 mL), dried with anhydrous sodium sulfate, and evaporated till dryness. The residual semicrystalline mass was suspended in ether (30 mL), the formed crystals were aspirated and washed with ether. There was obtained 2.200 g of a hygroscopic product.

Rf=0.62 (n-butanol:acetic acid:water=4:1:1)
M.p.: 220°-225° C.

IR (KBr) ν: 1765 vs, 1710 s, 1390 s, 1225 vs, 1045 s (cm$^{-1}$);

$^1$H NMR (DMSO-d$_6$) δ: 1.97 and 2.13 (2 s, C(CH$_3$)$_2$); 2.83 (dd, β C$_3$—H, J=14.7 Hz and J=2.5 Hz); 3.00 (dd, α C$_3$—H, J=14.7 Hz and J=5.3 Hz); 3.30-3.70 (b, H$_2$O); 4.37 (dd, C$_2$—H, J=2.5 Hz and J=5.3 Hz); 5.15 and 5.21 (2d, CH$_2$Ph, J=12.6 Hz); 7.33-7.40 (m, C$_6$H$_5$).

EXAMPLE 12

The methyl ester of 2R-1-(1'-benzyloxycarbonyl-2'-methyl-prop-1'-enyl)-4-oxo-azetidine-2-sulfonic acid (2.500 g, 7.08 mmole) and water (40 mL) were vigorously stirred at boiling temperature till the formation of a clear solution (about 30 minutes). Upon addition of ethyl acetate to the clear aqueous solution there was worked up, as described in Example 11.

Yield: 2.000 g of the product.

EXAMPLE 13

The mixture of the ethyl ester of 2R-1-(1'-benzyloxycarbonyl-2'-methyl-prop-1'-enyl)-4-oxo-azetidine-2-sulfonic acid (367 mg, 1 mmole) and water (10 mL) was vigorously stirred at boiling temperature till the formation of a clear solution. Upon addition of ethyl acetate to the cooled solution there was worked up, as described in Example 11.

Yield: 210 mg of the product.

EXAMPLE 14

The tert-butyl ester of 2R-1-(1'-benzyloxycarbonyl-2'-methyl-prop-1'-enyl)-4-oxo-azetidine-2-sulfonic acid (395 mg, 1 mmole) was stirred with water (10 mL) and worked up, as described in Example 11.

Yield: 180 mg of the product.

EXAMPLE 15

The methyl ester of 2R-1-(1'-benzyloxycarbonyl-2'-methyl-prop-1'-enyl)-4-oxo-azetidine-2-sulfonic acid (1.45 g, 4.1 mmole) was left in contact with atmospheric air at room temperature. The product was dissolved in a mixture of ethyl acetate (20 mL) and water (20 mL) and worked up, as described in Example 11.

Yield: 640 mg of the product.

EXAMPLE 16

The 2R-1-(1'-benzyloxycarbonyl-2'-methyl-prop-1'-enyl)-4-oxo-azetidine-2sulfinic acid (3.085 g, 9.55 mmole) was dissolved in ethyl acetate (20 mL), there was added 85% m-chloroperbenzoic acid (2,464 g, 12.2 mmole) and stirred for 4 hours at room temperature. Then a previously prepared solution of sodium sulfite (1.203 g, 9.55 mmole), which was dissolved in water (20 mL), was added drop-by-drop within 15 minutes into the reaction mixture. The reaction mixture was stirred for further 30 minutes. The layers were separated. The aqueous layer was once more extracted with ethyl acetate (20 mL). The combined ethyl acetate extracts were washed with water (20 mL). Upon addition of ethyl acetate (30 mL) to the combined aqueous portions the pH was adjusted to 7.5 with solid sodium hydrogen carbonate and further worked up, as in Example 11.

Yield: 2.300 g of the product.

EXAMPLE 17

The solution of 2R-1-(1'-benzyloxycarbonyl-2'-methyl-prop-1'-enyl)-4-oxo-azetidine-2-sulfinic acid (2.180 g, 6.75 mmole) in benzene (20 mL) was heated for 2 hours at boiling. The reaction mixture was evaporated into a dry residue in a water suction-pump vacuum. The dry residue was dissolved in a mixture of water (20 mL) and ethyl acetate (20 mL). The layers were separated and the aqueous layer was worked up as in Example 16.

Yield: 512 mg of the product.

2R-1-(1'-benzyloxycarbonyl-2'-methyl-prop-1'-enyl)-4-oxo-azetidine-2-sulfonic acid Example 18

The sodium salt of 2R-1-(1'-benzyloxycarbonyl-2'-methyl-prop-1'-enyl)-4-oxo-azetidine-2-sulfonic acid (1.080 g, 3 mmole) was dissolved in water (5 mL) and fed over Dowex 50W X 8. The acidic fraction was lyophilized, leaving an oily residue.

Yield: 980 mg.
$R_f = 0.62$ (n-BuOH:HAc:$H_2O$ = 4:1:1)
IR (film) $\nu$: 3450 s, 1760 vs, 1715 s, 1395 w, 1220 vs, 1040 s (cm$^{-1}$); $^1$H NMR (DMSO-$d_6$) $\delta$: 2.08 and 2.25 (2s, C(CH$_3$)$_2$); 2.91 (dd, $\beta$ C$_3$—H, J = 14.7 Hz and J = 2.3 Hz); 3.14 (dd, $\alpha$ C$_3$—H, J = 14.7 Hz and J = 5.0 Hz); 4.50 (dd, C$_2$—H, J = 2.3 Hz and J = 5.0 Hz); 5.10 (bs, SO$_2$OH and H$_2$O); 5.15 and 5.21 (2d, CH$_2$Ph, J = 12.6 Hz); 7.49 (m, C$_6$H$_5$) ppm.

Example 19

The methyl ester of 2R-1-(1'-benzyloxycarbonyl-2'-methyl-prop-1'-enyl)-4-oxoazetidine-2-sulfonic acid (0.200 g, 0.566 mmole) was suspended in water (5 mL) and vigorously stirred at boiling temperature till the formation of a clear solution. The clear aqueous solution was extracted with methylenechloride (2×5 mL). The aqueous portion was evaporated in a water suction-pump vacuum under addition of absolute ethanol.

Yield: 193 mg of the product.

2R-4-Oxo-azetidine-2-sulfonic acid

Example 20

The sodium salt of 2R-1-(1'-benzyloxycarbonyl-2'-methyl-prop-1'-ethyl)-4-oxo-azetidine-2-sulfonic acid (1.500 g, 4.15 mmole) was dissolved in water (30 mL), cooled to 0° C. and at this temperature the drop-by-drop addition of an aqueous solution of potassium permanganate was started, till the stabilization of the permanganate violet color. The acidity of the reaction mixture was kept during the addition by means of acetic acid within the limiting values of pH 5-6. The manganese dioxide precipitate was aspirated and washed with water. The clear colorless aqueous solution was evaporated to dryness in a vacuum under addition of absolute ethanol. Once more absolute ethanol was added (30 mL). The separated precipitate was aspirated and washed with absolute ethanol. The residue was dissolved in water (20 mL) and fed through a column filled with Dowex 50W X 8, and lyophilized. The lyophilized residue was suspended in ethyl acetate (20 mL). The ethyl acetate was decanted, whereas, the residual crystalline mass was washed with ethyl acetate (2×10 mL). The residual crystals were dried in a water suction-pump vacuum. There was obtained 480 mg of a white, highly hygroscopic product.

$R_f = 0.45$ (n-butanol:acetic acid:water = 4:1:1)
$^1$H NMR (DMSO-$d_6$) $\delta$: 2.82 (dd, $\beta$ C$_3$—H, J = 14.5 Hz and J = 1.9 Hz); 3.07 (dd, $\alpha$ C$_3$—H, J = 14.5 Hz and J = 50 Hz); 3.37 (bs, SO$_2$OH and H$_2$O); 4.20 (dd, C$_2$—H, J = 1.9 Hz and J = 5.0 Hz); 8.37 (s, NH) (ppm).

EXAMPLE 21

The methyl ester of 2R-4-oxo-azetidine-2-sulfonic acid (1.650 g, 10 mmole) was suspended in water (10 mL) and heated under boiling till the formation of a clear aqueous solution. The aqueous solution was extracted with ethyl acetate (2×10 mL) and lyophilized. The residual mass was worked up, as described in Example 20.

Yield: 120 mg of the product.

Sodium salt of 2R-3,3-dibromo-1-(1'-benzyloxycarbonyl-2'-methyl-prop-1'-enyl)-4-oxo-azetidine-2-sulfonic acid

EXAMPLE 22

Upon addition of 85% m-chloroperbenzoic acid (1.31 g, 6.5 mmole) to the solution of 2R-3,3-dibromo-1-(1'-benzyloxycarbonyl-2'-methyl-prop-1'-enyl)-4-oxo-azetidine-2-sulfinic acid (3.128 g, 6.5 mmole) in chloroform (30 mL) there was stirred for 20 minutes at −10° C. There was kept stirring for one additional hour at room temperature. Upon addition of a 1M solution of sodium bisulfite (30 mL, 30 mmole) to the reaction mixture, the layers were separated, and the chloroform evaporated to dryness. The obtained residue was suspended in water (4.0 mL) and the precipitate was aspirated. Ethyl acetate (30 mL) was added to the aqueous filtrate and the pH was adjusted to 7.5-8 with solid sodium hydrogen carbonate. Upon addition of sodium chloride till saturation the layers were separated, whereas, the aqueous portion was once more extracted with ethyl acetate (2×20 mL). The combined ethyl acetate layers were thoroughly shaken with a saturated aqueous solution of sodium chloride, dried with anhydrous sodium sulfate and evaporated till dryness. There was obtained 1.379 g of the hygroscopic product.

$R_f = 0.70$ (ethyl acetate:methanol = 3:1)
IR (film) $\nu$: 3500 bs, 1795 vs, 1710 s, 1635 m, 1390 w, 1370 w, 1220 vs, 1050 s (cm$^{-1}$);
$^1$H NMR (CDCl$_3$) $\delta$: 1.99 and 2.11 (2s, C(CH$_3$)$_2$); 5.20 (s, CH$_2$Ph); 5.27 (s, C$_2$—H) and 7.31 (s, C$_6$H$_5$) ppm.

Tetrabutylammonium salt of 2R-3,3-dibromo-1-(1'-benzyloxycarbonyl-2'-methyl-prop-1'-enyl)-4-oxo-azetidine-2-sulfonic acid

EXAMPLE 23

The sodium salt of 2R-3,3-dibromo-1-(1'-benzyloxycarbonyl-2'-methyl-prop-1'-enyl)-4-oxo-azetidine-2-sulfonic acid (0.259 g, 0.5 mmole), was dissolved in water (10 mL), there was added tetrabutylammonium hydrogen sulfate (0.169 g, 0.5 mmole), dissolved in methylenechloride (10 mL), and stirred for 1 hour at room temperature. The methylenechloride layer was separated, and the water extracted with a new portion of methylenechloride (2×15 mL). The combined organic layers were dried with anhydrous sodium sulfate and evaporated to dryness. There was obtained 0.281 g of an oily product.

$R_f = 0.70$ (ethyl acetate:methanol = 3:1)
IR (film) $\nu$: 3600–3300 b, 1790 vs, 1730 s, 1615 m, 1465 s, 1370 vs, 1225 vs, 1050 s (cm$^{-1}$);
$^1$H NMR (CDCl$_3$) $\delta$: 0.85–1.60 (m, 28H); 2.10 and 2.19 (2 s, C(CH$_3$)$_2$); 3.12–3.18 (m, 8H); 5.01 (dd, CH$_2$Ph); 5.25 (s, C$_2$—H) and 7.29–7.31 (m, C$_6$H$_5$) ppm.

2R-3,3-Dibromo-1-(1'-benzyloxycarbonyl-2'-methyl-prop-1'-enyl)-4-oxo-azetidine-2-sulfonic acid

EXAMPLE 24

The sodium salt of 2R-3,3-dibromo-1-(1'-benzyloxycarbonyl-2'-methyl-prop-1'-enyl)-4-oxo-azetidine-2-sulfonic acid (0.519 g, 1 mmole) was dissolved in water (10 mL) and fed through a column of Dowex 50W X 8. Upon lyophilization of the obtained acidic fractions there was obtained 0.376 g of a white, highly hygroscopic powder.

Rf=0.70 (ethyl acetate:methanol=3:1)

IR (film)$\nu$:3600-3300 b, 1797 vs, 1735 s, 1710 s, 1395 s, 1370 s, 1220 vs, 1050 s (cm$^{-1}$)

$^1$H NMR (DMSO-d$_6$) $\delta$: 2.09 and 2.30 (2 s, C(CH$_3$)$_2$); 3.80 (s, SO$_2$OH and H$_2$O); 4.98 (s, C$_2$—H); 5.29 (dd, CH$_2$Ph) and 7.50 (m, C$_6$H$_5$) ppm.

EXAMPLE 25

The methyl ester of 2R-3,3-dibromo-1-(1'-benzyloxycarbonyl-2'-methyl-prop-1'-enyl)-4-oxo-azetidine-2-sulfonic acid (0.511 g, 1 mmole) was dissolved in methylenechloride (10 mL), there was added triethylamine (0.28 mL, 2 mmole) and stirred for 4 hours at room temperature. The reaction mixture was evaporated to dryness, the residue was dissolved in water (10 mL) and fed through Dowex 50W X 8, whereas, the acidic eluate was lyophilized.

The yield: 0.346 g of the product.

EXAMPLE 26

The methyl ester of 2R-3,3-dibromo-1-(1'-benzyloxycarbonyl-2'-methyl-prop-1'-enyl)-4-oxo-azetidine-2-sulfonic acid (0.511 g, 1 mmole) was dissolved in a mixture of water (25 mL) and ethyl acetate (25 mL), and stirred at boiling temperature for 4 hours. The layers were separated and the aqueous layer was extracted with ethyl acetate (3×25 mL), dried with anhydrous sodium sulfate and evaporated to dryness. There was obtained 0.474 g of a foamy product. The crude product was fed through a silica gel 60 F. column with a solvent system ethyl acetate-methanol (3:1). The evaporated residue was dissolved in water (10 mL) and fed over Dowex 50W X 8, whereas, the acidic fraction was lyophilized. There was obtained 0.195 g of the product.

2R-3,3-Dibromo-4-oxo-azetidine-2-sulfonic acid

Example 27

The sodium salt of 2R-3,3-dibromo-1-(1'-benzyloxycarbonyl-2'-methyl-prop-1'-enyl)-4-oxo-azetidine-2-sulfonic acid (0.519 g, 1 mmole) was dissolved in water (5 mL), cooled to 0°-5° C., whereupon there was added drop-by-drop an aqueous solution (4%) of potassium permanganate till the stabilization of the pink color. The solution was filtered over diatomaceus earth and the obtained filtrate was fed over Dowex 50W X 8. The acidic fractions were lyophilized. There was obtained 0.231 g of the hygroscopic product.

Rf=0.45 (ethyl acetate:methanol=3:1)

IR (film) $\nu$: 3600-3300 b, 1775 vs, 1725 s, 1220 s (cm$^{-1}$);

$^1$H NMR (DMSO-d$_6$) $\delta$: 5.27 (s, C$_2$—H) and 9.66 (s, NH) ppm.

Sodium salt of 2R,3S-3-bromo-1-(1'-benzyloxycarbonyl-2'-methyl-prop-1'-enyl)-4-oxo-azetidine-2-sulfonic acid

Example 28

The 2R,3S-3-bromo-1-(1'-benzyloxycarbonyl-2'-methyl-prop-1'-enyl)-4-oxo-azetidine-2-sulfinic acid (0.201 g, 0.5 mmole) was dissolved in chloroform (5 mL), cooled to −10° C. and there was added 85% m-chloroperbenzoic acid (0.1 g, 0.5 mmole), stirred for 20 minutes and then 1 additional hour at room temperature. Upon addition of a 1M solution of sodium bisulfite (3 mL, 3 mmole) to the reaction, the layers were separated and the chloroform layer was evaporated to dryness. Water (1.5 mL) was added to the evaporated residue, the precipitate was aspirated, whereas, ethyl acetate (5 mL) was added to the aqueous portion and the pH was adjusted to 7.5-8 with solid sodium hydrogen carbonate. The aqueous portion was saturated with sodium chloride and the layers were separated. The aqueous layer was once more extracted with ethyl acetate (3×5 mL). The combined ethyl acetate extracts were washed with a saturated solution of sodium chloride and evaporated to dryness. There was obtained 0.07 g of a white, foamy product.

Rf=0.68 (ethyl acetate:methanol=3:1)

$^1$H NMR (DMSO-d$_6$) $\delta$: 2.10 and 2.30 (2 s, C(CH$_3$)$_2$); 4.62 (d, C$_2$—H, J=1.8 Hz); 4.93 (d, C$_3$—H, J=1.8 Hz); 5.31 (s, CH$_2$Ph) and 7.20 (m, C$_6$H$_5$) ppm.

2R,3S-3-bromo-1-(1'-benzyloxycarbonyl-2'-methyl-prop-1'-enyl)-4-oxo-azetidine-2-sulfonic acid

EXAMPLE 29

The sodium salt of 2R,3S-3-bromo-1-(1'-benzyloxycarbonyl-2'-methyl-prop-1'-enyl)-4-oxo-azetidine-2-sulfonic acid (50 mg) was dissolved in water (5 mL), and fed through a column of Dowex 50W X 8. The acidic fractions were lyophilized. There was obtained 38 mg of a hygroscopic substance.

Rf=0.68 (ethyl acetate:methanol=3:1)

IR (film) $\nu$: 3600-3300 b, 1790 vs, 1730 s, 1705 s, 1630 w, 1395 m, 1370 s, 1330 s, 1220 vs, 1035 s (cm$^{-1}$);

$^1$H NMR (DMSO-d$_6$) $\delta$: 1.96 and 2.17 (2 s, C(CH$_3$)$_2$); 4.50 (d, C$_2$—H, J=1.2 Hz); 4.84 (d, C$_3$—H, J=1.2 Hz); 5.18 (s, CH$_2$Ph) and 7.36 (s, C$_6$H$_5$) ppm.

EXAMPLE 30

To the solution of the methyl ester of 2R-3,3-dibromo-1-(1'-benzyloxycarbonyl-2'-methyl-prop-1'-enyl)-4-oxo-azetidine-2-sulfonic acid (0.1 g, 0.2 mmole) in isopropanol (5 mL), there was added AgNO$_3$ (0.135 g, 0.8 mmole) and stirred under boiling in a nitrogen stream. After 1 hour the solution was filtered over diatomaceus earth and the filtrate was evaporated to dryness. Methylenechloride (5 mL) was added to the evaporated residue, and the obtained precipitate was aspirated, whereas, the filtrate was once more evaporated into a dry residue. The obtained residue was fed through a column of Dowex 50W X 8 and the acidic fraction was lyophilized. The crude product was fed through a silica gel column with a solvent system ethyl acetate-methanol (3:1). The fraction of an Rf value of 0.68 was retained.

2R,3R-3-Bromo-1-(1'-benzyloxycarbonyl-2'-methyl-prop-1'-enyl)-4-oxo-azetidine-2-sulfonic acid

EXAMPLE 31

Upon further elution of the crude product of Example 30 with a solvent system ethyl acetate-methanol (3:1) there was isolated a substance of an Rf value of 0.63.

IR (film) ν: 3600–3300 b, 1790 vs, 1730 s, 1705 s, 1630 w, 1395 m, 1370 s, 1300 s, 1220 vs, 1035 s, 700 m (cm$^{-1}$);

$^1$H NMR (DMSO-d$_6$) δ: 1.98 and 2.14 (2 s, C(CH$_3$)$_2$); 4.64 (d, C$_2$—H, J=5.3 Hz); 5.18 (s, CH$_2$Ph); 5.34 (d, C$_3$—H, J=5.3 Hz) and 7.36 (s, C$_6$H$_5$) ppm.

We claim:

1. 4-Oxo-azetidine-2-sulfonic acids and their salts of the formula I

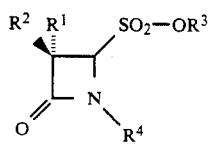

wherein the radicals have the meanings:

R$^1$=hydrogen, halogen, phenylacetamido;

R$^2$=hydrogen, halogen, phenylacetamido, phenoxyacetamido, phthalimido, 5-methyl-3-o-chlorophenyl-isoxazole-4-carboxamido;

R$^3$=hydrogen, alkali metal, alkaline earth metal, tetrabutyl ammonium group;

R$^4$=hydrogen, SO$_2$O$^-$$^+$NBu$_4$-n, (CH$_3$)$_2$C=C—COOCH$_3$, (CH$_3$)$_2$C=C—COOCH$_2$—C$_6$H$_5$, (CH$_3$)$_2$C=C—COOCH$_2$—C$_6$H$_4$—NO$_2$-p, (CH$_3$)$_2$C=C—COOCH$_2$—C$_6$H$_4$—CH$_3$-m.

2. A substance as claimed in claim 1, wherein R$^1$ stands for hydrogen, R$^2$ stands for phthalimido, R$^3$ stands for hydrogen and R$^4$ stands for (CH$_3$)$_2$C=C—COOCH$_2$C$_6$H$_4$NO$_2$-p.

3. A substance as claimed in claim 1, wherein R$^1$ stands for hydrogen, R$^2$ stands for phenylacetamido, R$^3$ stands for hydrogen and R$^4$ stands for (CH$_3$)$_2$C=C—COOCH$_2$C$_6$H$_4$NO$_2$-p.

4. A substance as claimed in claim 1, wherein R$^1$ stands for hydrogen, R$^2$ stands for phenylacetamido, R$^3$ stands for sodium, and R$^4$ stands for hydrogen.

5. A substance as claimed in claim 1, wherein R$^1$ stands for hydrogen, R$^2$ stands for phenylacetamido, R$^3$ stands for tetrabutylammonium, and R$^4$ stands for hydrogen.

6. A substance as claimed in claim 1, wherein R$^1$ stands for hydrogen, R$^2$ stands for phenylacetamido, R$^3$ stands for tetrabutylammonium, and R$^4$ stands for SO$_2$O$^-$$^+$NBu$_4$-n.

7. A substance as claimed in claim 1, wherein R$^1$ stands for hydrogen, R$^2$ stands for phenoxyacetamido, R$^3$ stands for hydrogen, and R$^4$ stands for hydrogen.

8. A substance as claimed in claim 1, wherein R$^1$ stands for hydrogen, R$^2$ stands for phenoxyacetamido, R$^3$ stands for hydrogen, and R$^4$ stands for (CH$_3$)$_2$C=C—COOCH$_3$.

9. A substance as claimed in claim 1, wherein R$^1$ stands for hydrogen, R$^2$ stands for phenoxyacetamido, R$^3$ stands for tetrabutylammonium, and R$^4$ stands for hydrogen.

10. A substance as claimed in claim 1, wherein R$^1$ stands for hydrogen, R$^2$ stands for 5-methyl-3-o-chlorophenyl-isoxazole-4-carboxamido, R$^3$ stands for hydrogen and R$^4$ stands for (CH$_3$)$_2$C=C—COOCH$_2$C$_6$H$_4$CH$_3$-m.

11. A substance as claimed in claim 1, wherein R$^1$ stands for phenylacetamido, R$^2$ stands for hydrogen, R$^3$ stands for tetrabutylammonium, and R$^4$ stands for hydrogen.

12. A substance of formula I as claimed in claim 1, wherein each of R$^1$, R$^2$, R$^3$ and R$^4$ stands for hydrogen.

13. A substance of formula I as claimed in claim 1, wherein each of R$^1$, R$^2$ and R$^4$ stands for hydrogen, and R$^3$ stands for sodium.

14. A substance of formula I as claimed in claim 1, wherein each of R$^1$, R$^2$ and R$^3$ stands for hydrogen, and R$^4$ stands for (CH$_3$)$_2$C=COOCH$_2$—C$_6$H$_5$.

15. A substance of formula I as claimed in claim 1, wherein each of R$^1$ and R$^2$ stands for hydrogen, R$^3$ stands for sodium and R$^4$ stands for (CH$_3$)$_2$C=C—COOCH$_2$—C$_6$H$_5$.

16. A substance of formula I as claimed in claim 1, wherein each of R$^1$ and R$^2$ stands for hydrogen, R$^3$ stands for tetrabutylammonium, and R$^4$ stands for (CH$_3$)$_2$C=C—COOCH2—C$_6$H5.

17. A substance of formula I as claimed in claim 1, wherein each of R$^1$, R$^2$ and R$^3$ stands for hydrogen, and R$^4$ stands for (CH$_3$)$_2$C=C—COOCH$_3$.

18. A substance of formula I as claimed in claim 1, wherein each of R$^1$ and R$^2$ stands for bromine, and each of R$^3$ and R$^4$ stands for hydrogen.

19. A substance of formula I as claimed in claim 1, wherein each of R$^1$ and R$^2$ stands for bromine, R$^3$ stands for hydrogen, and R$^4$ stands for (CH$_3$)$_2$C=C—COOCH$_2$—C$_6$H$_5$.

20. A substance of formula I as claimed in claim 1, wherein each of R$^1$ and R$^2$ stands for bromine, R$^3$ stands for tetrabutylammonium, and R$^4$ stands for (CH$_3$)$_2$C=C—COOCH$_2$—C$_6$H$_5$.

21. A substance of formula I as claimed in claim 1, wherein each of R$^1$ and R$^2$ stands for bromine, R$^3$ stands for sodium, and R$^4$ stands for (CH$_3$)$_2$C=C—COOCH$_2$—C$_6$H$_5$.

22. A substance of formula I as claimed in claim 1, wherein R$^1$ stands for hydrogen, R$^2$ stands for bromine, R$^3$ stands for hydrogen, and R$^4$ stands for (CH$_3$)$_2$C=C—COOCH$_2$—C$_6$H$_5$.

23. A substance of formula I as claimed in claim 1, wherein R$^1$ stands for bromine, and each of R$^2$ and R$^3$ stands for hydrogen, and R$^4$ stands for (CH$_3$)$_2$C=C—COOCH$_2$—C$_6$H$_5$.

24. A substance of formula I as claimed in claim 1, wherein R$^1$ stands for bromine, R$^2$ stands for hydrogen, R$^3$ stands for sodium and R$^4$ stands for (CH$_3$)$_2$C=C—COOCH$_2$—C$_6$H$_5$.

25. A pharmaceutical composition comprising the compound of claim 1 in an antibacterial effective amount and a carrier.

* * * * *

UNITED STATES PATENT AND TRADEMARK OFFICE
CERTIFICATE OF CORRECTION

PATENT NO. : 5,250,525
DATED : October 5, 1993
INVENTOR(S) : Kovacevic et al

It is certified that error appears in the above-identified patent and that said Letters Patent is hereby corrected as shown below:

On the title page, item [73]

Assignee: PLIVA HANDELS GmbH, Germany and
PLIVA, Croatia

Signed and Sealed this

Sixteenth Day of December, 1997

Attest:

BRUCE LEHMAN

Attesting Officer

Commissioner of Patents and Trademarks